United States Patent
Liu et al.

(10) Patent No.: US 9,023,590 B2
(45) Date of Patent: May 5, 2015

(54) DEEP-ULTRAVIOLET CHEMICALLY-AMPLIFIED POSITIVE PHOTORESIST

(71) Applicant: BOE Technology Group Co., Ltd., Beijing (CN)

(72) Inventors: Lu Liu, Beijing (CN); Jianshe Xue, Beijing (CN); Guanbao Hui, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 31 days.

(21) Appl. No.: 14/067,186

(22) Filed: Oct. 30, 2013

(65) Prior Publication Data

US 2014/0120474 A1 May 1, 2014

(30) Foreign Application Priority Data

Oct. 31, 2012 (CN) .......................... 2012 1 0429479

(51) Int. Cl.
| | | |
|---|---|---|
| *G03F 7/029* | (2006.01) | |
| *C07C 61/29* | (2006.01) | |
| *G03F 7/039* | (2006.01) | |
| *G03F 7/38* | (2006.01) | |

(52) U.S. Cl.
CPC ............ *G03F 7/0392* (2013.01); *G03F 7/0295* (2013.01); *G03F 7/38* (2013.01); *C07C 2103/90* (2013.01); *C07C 61/29* (2013.01)

(58) Field of Classification Search
CPC .... G03F 7/0295; C07C 61/29; C07C 2103/90
USPC ........................ 430/288.1; 562/498, 509, 510
See application file for complete search history.

(56) References Cited

U.S. PATENT DOCUMENTS

| 5,480,762 A * | 1/1996 | Toyama et al. ............... 430/302 |
| 6,265,131 B1 | 7/2001 | Chang et al. |
| 2002/0031719 A1 | 3/2002 | Nakamura et al. |

FOREIGN PATENT DOCUMENTS

| CN | 1407406 A | 4/2003 |
| CN | 1701280 A | 11/2005 |
| CN | 102156385 A | 8/2011 |
| JP | 2005010213 A | 1/2005 |

OTHER PUBLICATIONS

Chinese Office Action and translation regarding Application No. 201210429479 dated Aug. 13, 2013. Translation provided by Dragon Intellectual Property Law Firm.
Extended European Search Report regarding Application No. 13190478.1-1564, dated Feb. 6, 2014.
Liyuan Wang et al: "Studies on a cross-linking type positive 193nm photoresist material", vol. 6153, Mar. 9, 2006, pp. 615329-615329-8.
Werner Herz et al "Resin acids, XIX, Structure and sterochemistry of adducts of levopimaric acid with cyclopentenone and 1-cyclepentene-3, 5-dione. Favorski reaction of an enedione epoxide", The Journal of Organic Chemistry, vol. 34, No. 12, Dec. 1, 1969, pp. 4016-4023.
Database WPI, Week 201175, Thomson Scientific, London, GB; AN 2011-L60313, XP002718584.

\* cited by examiner

*Primary Examiner* — John Chu
(74) *Attorney, Agent, or Firm* — Harness, Dickey & Pierce, P.L.C.

(57) ABSTRACT

The invention discloses a deep-ultraviolet chemically-amplified positive photoresist. The deep-ultraviolet chemically-amplified positive photoresist according to one embodiment of the invention includes a cyclopentenyl pimaric acid, a divinyl ether, a photoacid generator and an organic solvent. The deep-ultraviolet chemically-amplified positive photoresist according to the invention has a good sensitivity and a good transparency.

20 Claims, No Drawings

DEEP-ULTRAVIOLET CHEMICALLY-AMPLIFIED POSITIVE PHOTORESIST

CROSS REFERENCE

The present application claims priority to the Chinese application No. 201210429479.1 filed on Oct. 31, 2012, entitled with "deep-ultraviolet chemically-amplified positive photoresist", the entire contents of which are incorporated herein by reference.

The present invention relates to the field of photosensitive materials, and in particular, to a deep-ultraviolet chemically-amplified positive photoresist.

DESCRIPTION OF THE PRIOR ART

The concept of "Chemical Amplification" was first put forward by Ito, et al, from IBM in early 1980s. As a novel photoresist, the chemically amplified resist is different from a common photoresist. For a common photoresist, each time a photon is absorbed, there occurs at most one crosslinking or decomposition reaction, thus the efficiency is low. However, for a chemically amplified resist, it is generally consisted of a photoacid generator (PAG) and an acid-sensitive film-forming resin, and during exposure, the photoacid generator is decomposed to generate a strong acid, which catalyzes the decomposing or crosslinking of the acid-sensitive resin, and because a catalyst may be used circularly in the reaction, the efficiency will be very high. The 248 nm photoresist is a resist to which the concept of "chemical amplification" is first applied; and usually, a derivative of poly(para-hydroxystyrene) is employed as the film-forming resin, and an aryliodonium salt or an arylsulfonium salt is employed as the photoacid generator. Generally, it requires that the film-forming resin should have a high transparency at 248 nm; poly(para-hydroxystyrene) and the derivatives thereof have a good transparency at 248 nm themselves, but if impurities are contained in the polymer, the transparency of the resin will be lowered greatly, thus this kind of photoresist has a strict requirement on the purity of poly(para-hydroxystyrene), and the manufacturing process is complex.

SUMMARY OF THE INVENTION

One object of the invention is to provide a deep-ultraviolet chemically-amplified positive photoresist with a good sensitivity.

The deep-ultraviolet chemically-amplified positive photoresist according to the invention comprises a cyclopentenyl pimaric acid, a divinyl ether, a photoacid generator and an organic solvent, wherein the cyclopentenyl pimaric acid is represented by the following formula:

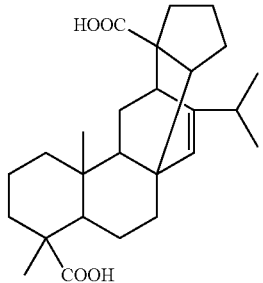 [SMILES: CC(C)C1=CC23CCC4C(C)(C(=O)O)CCCC4(C)C2CC1C1(C(=O)O)CCCC31]

Preferably, the divinyl ether is at least one selected from ethylene glycol divinyl ether, propylene glycol divinyl ether, butylene glycol divinyl ether, diethylene glycol divinyl ether, 1,3-di-(ethyleneoxy ethoxy)benzene, 1-methyl-1,2-diethyleneoxy ethane and 1,7-di-(ethyleneoxy ethoxy)naphthalene, and more preferably, the divinyl ether is ethylene glycol divinyl ether, propylene glycol divinyl ether, diethylene glycol divinyl or, 1,3-di-(ethyleneoxy ethoxy)benzene.

Preferably, the photoacid generator is at least one selected from triphenylsulfonium trifluoromethanesulphonate, S-(2-naphthoyl)methyltetrahydrothiophenium trifluoromethanesulphonate, tri(4-methylphenyl)sulfonium trifluoromethanesulphonate, heptafluoropropane sulphonate, (4-methylphenyl)diphenyl trifluoromethanesulphonate, (p-tert-butylphenyl)diphenylsulfonium trifluoromethanesulphonate and tri(p-tert-butylphenyl)sulfonium trifluoromethanesulphonate, and more preferably, the photoacid generator is triphenylsulfonium trifluoromethanesulphonate.

Preferably, the organic solvent is at least one selected from acetone, methylethylketone, cyclohexanone, ethylene glycol monoethyl ether, ethylene glycol monoacetate, diethylene glycol, propylene glycol, propylene glycol monoacetate, methyl lactate, propylene glycol methyl ether acetate and ethylene glycol methyl ether acetate.

Preferably, the mole ratio of the cyclopentenyl pimaric acid to the divinyl ether is in the range of from about 5:4 to about 1:2, and more preferably, in the range of from about 1:1 to about 2:3.

Preferably, the photoacid generator is in the range of from about 0.5% to about 5% by mass of the total mass of the cyclopentenyl pimaric acid and the divinyl ether, and more preferably, in the range of from about 1.0% to about 3.0%.

Preferably, the total mass of the photoacid generator, the cyclopentenyl pimaric acid and the divinyl ether is in the range of from about 10% to about 35% by mass of the organic solvent, and more preferably, in the range of from about 10% to about 30%.

Preferably, the cyclopentenyl pimaric acid is prepared according to the process which comprises the following steps:

Heating a gum resin to a temperature of from about 210 to about 250° C., adding cyclopentenecarboxylic acid dropwise in a nitrogen atmosphere, carrying out the reaction at the temperature of from about 210° C. to about 250° C. after adding of cyclopentenecarboxylic acid is completed, and obtaining a crude product of cyclopentenyl pimaric acid after the reaction is completed; and further washing the crude product with a detergent and thus obtaining a product of cyclopentenyl pimaric acid.

Preferably, the detergent is at least one selected from the group consisting of carbon tetrachloride, trichloromethane, acetone, cyclohexanone and ether.

Another object of the invention is to provide a cyclopentenyl pimaric acid.

The structural formula of the cyclopentenyl pimaric acid according to the invention is as follows:

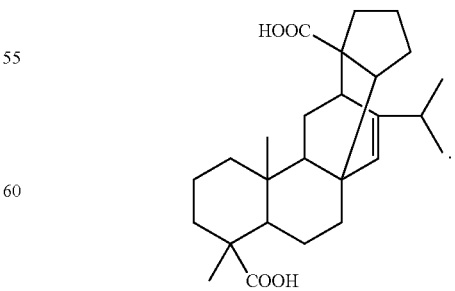

The softening temperature of the cyclopentenyl pimaric acid is in the range of from about 130° C. to about 132° C., and the acid number is about 295 mg KOH/g.

According to the embodiment of the present invention, a diacid with a large alicyclic ring structure, i.e., cyclopentenyl pimaric acid, is prepared from abietic acid and cyclic olefin acid via a Diels-Alder (D-A) reaction. Since the diacid does not contain a benzene ring structure, it has a good transparency in the deep-ultraviolet band, and thereby having a good sensitivity.

A deep-ultraviolet chemically-amplified positive photoresist can consist of the cyclopentenyl pimaric acid according to the invention, the divinyl ether and the photoacid generator. The deep-ultraviolet chemically-amplified positive photoresist has a good sensitivity.

DETAILED DESCRIPTION OF THE PREFERRED EMBODIMENTS

Synthesization of Cyclopentenyl Pimaric Acid

A gum resin is added to a four-necked flask equipped with a stirring unit and a condensing unit and heated to a temperature of from about 210 to about 250° C. while a nitrogen gas is introduced into the four-necked flask. Then cyclopentenecarboxylic acid is added dropwise slowly, and the adding time is controlled in the range of from about 2 hours to about 5 hours. After adding of cyclopentenecarboxylic acid is completed, the mixture is continued to react at the temperature of from about 210° C. to about 250° C. for about 3-5 hours. A crude product of cyclopentenyl pimaric acid is obtained after cooling down and discharging from the flask. The product is washed for one or more times with a detergent, and preferably, the detergent is at least one selected from the group consisting of carbon tetrachloride, trichloromethane, acetone, cyclohexanone and ether, and then a final product, i.e., cyclopentenyl pimaric acid, is obtained.

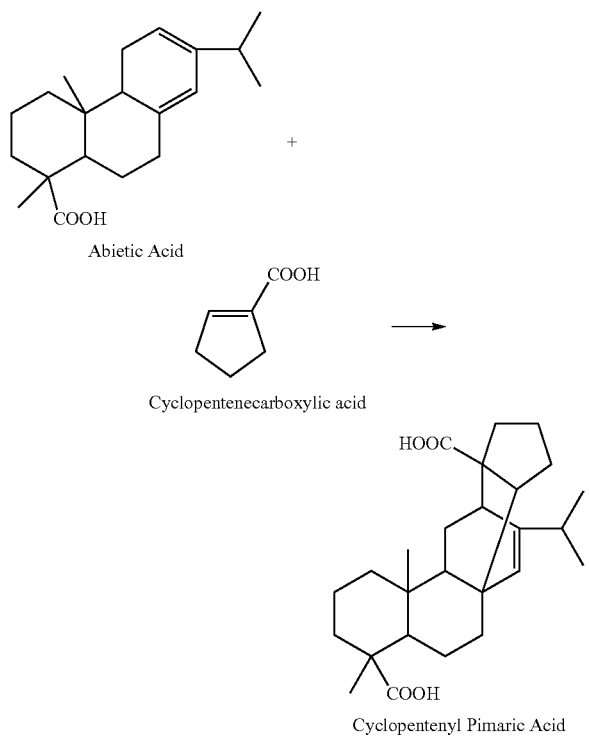

Synthesization Example 1

50 g of gum resin is added to a four-necked flask equipped with a stirring unit and a condensing unit and heated to a temperature of about 230° C. while a nitrogen gas is introduced into the flask. Then 17 g of cyclopentenecarboxylic acid is added dropwise slowly, and adding time is controlled within 2 hours. After adding of cyclopentenecarboxylic acid is completed, the mixture is continued to react at the temperature of about 230° C. for about 3 hours, then a crude product of cyclopentenyl pimaric acid is obtained by cooling down and discharging from the flask. The crude product is washed once with carbon tetrachloride. The washed product is dried and analyzed. As a result, the softening temperature is in the range of from about 130° C. to about 132° C., and the acid number is about 295 mg KOH/g. The content of the target product measured by High Performance Liquid Chromatography (HPLC) is about 75% by mass.

Synthesization Example 2

50 g of gum resin is added into a four-necked flask equipped with a stirring unit and a condensing unit and heated to a temperature of about 210° C. while a nitrogen gas is introduced into the flask. Then 17 g of cyclopentenecarboxylic acid is added dropwise slowly, and adding time is controlled within 5 hours. After adding of cyclopentenecarboxylic acid is completed, the mixture is continued to react at a temperature of about 210° C. for about 4 hours, then a crude product of cyclopentenyl pimaric acid is obtained by cooling down and discharging from the flask. The crude product is washed once with trichloromethane. The washed product is dried and analyzed. As a result, the softening temperature is in the range of from about 130° C. to about 132° C., and the acid number is 295 mg KOH/g. The content of the target product measured by HPLC is about 75% by mass.

Synthesization Example 3

50 g of gum resin is added to a four-necked flask equipped with a stirring unit and a condensing unit and heated to a temperature of about 250° C. while a nitrogen gas is introduced into the flask. Then 17 g of cyclopentenecarboxylic acid is added dropwise slowly, and adding time is controlled within 3 hours. After adding of cyclopentenecarboxylic acid is completed, the mixture is continued to react at a temperature of about 250° C. for about 5 hours, then a crude product of cyclopentenyl pimaric acid is obtained by cooling down and discharging from the flask. The crude product is washed once with acetone. The washed product is dried and analyzed. As a result, the softening temperature is in the range of from about 130° C. to about 132° C., and the acid number is 295 mg KOH/g. The content of the target product measured by HPLC is about 75% by mass.

In a solid film, cyclopentenyl pimaric acid may react with divinyl ether under a heated condition (above 80° C.)., and the resultant product is indissoluble in the dilute alkaline solution. The product thus produced may be decomposed rapidly at a temperature higher than 100° C. under the catalysis of a strong acid generated by a photoacid generator, so that it becomes dissoluble in the dilute alkaline solution. Thus, a positive photoresist can be made of the diacid, the divinyl ether and the acid generator.

Optional Divinyl Ether: Ethylene glycol divinyl ether (EGDE), propylene glycol divinyl ether (PGDE), butylene glycol divinyl ether (BGDE), diethylene glycol divinyl ether (DEGDE), 1,3-di-(ethyleneoxy ethoxy)benzene (1,3-

DEEB), 1-methyl-1,2-diethyleneoxy ethane (1-M-1,2-DE) and 1,7-di-(ethyleneoxy ethoxy)naphthalene (1,7-DEN), etc., and the above divinyl ethers may be used singly or in a combination of two or more.

Optional Photoacid Generator: Any substance, which is typically used in the traditional chemically-amplified photoresist as an acid generator, may be used as the acid generator in the present invention, and preferred acid generators comprise triphenylsulfonium trifluoromethanesulphonate, S-(2-naphthoyl)methyltetrahydrothiophenium trifluoromethanesulphonate, tri(4-methylphenyl)sulfonium trifluoromethanesulphonate, heptafluoropropane sulphonate, (4-methylphenyl)diphenyl trifluoromethanesulphonate, (p-tert-butylphenyl)diphenylsulfonium trifluoromethanesulphonate and tri(p-tert-butylphenyl)sulfonium trifluoromethanesulphonate, etc., and the above acid generators may be used singly or in a combination of two or more.

Organic solvent: The organic solvent may be any solvent in which the components of a photoresist can be dissolved to generate a homogeneous solution. The preferred solvents comprise acetone, methylethylketone (MEK), cyclohexanone (CH), ethylene glycol monoethyl ether (EGME), ethylene glycol monoacetate (EGMA), diethylene glyol (DEG), propylene glycol (PG), propylene glycol monoacetate (PGMA), methyl lactate (ML), propylene glycol methyl ether acetate (PGMEA) and ethylene glycol methyl ether acetate (EGMEA), etc., and the above solvents may be used singly or in a combination of two or more.

EXAMPLES 1-10

Positive Photoresist

A positive photoresist will be prepared according to the composition listed in the table 1 below.

In order to form a photoresist pattern by using the positive photoresist according to the embodiment of the invention, the conventional photoetching steps are carried out as follows, wherein the cyclopentenyl pimaric acid used in examples 1-8 is obtained in the synthesization example 1, the cyclopentenyl pimaric acid used in examples 9-11 is obtained in the synthesization example 2, and the cyclopentenyl pimaric acid used in examples 12-13 is obtained in the synthesization example 3:

First of all, a photoresist is coated on a substrate, for example, a silicon wafer, via a spin coater to form a photoresist layer, and then it is prebaked at 60° C. for 90 seconds;

Next, the photoresist is exposed under a mask plate with a preset pattern, and it is post-baked at 100° C. for 2 minutes after being exposed on the deep-ultraviolet of 248 nm.

Finally, the photoresist coating layer exposed is developed, and a 0.38 wt % tetramethyl ammonium hydroxide is used as the liquid developer, the temperature of the liquid developer is 25° C., and the developing time is 60 seconds.

TABLE 1

| Embodiment | Cyclopentenyl Pimaric Acid (g) | Divinyl Ether (g) | Triphenylsulfonium Trifluoromethanesulphonate (g) | Solvent (g) | Sensitivity mJ/cm$^{-2}$ |
|---|---|---|---|---|---|
| Embodiment 1 | 2 | EGDE 0.55 | 0.051 | PGMEA 13 | 20 |
| Embodiment 2 | 2 | DEGDE 0.76 | 0.055 | PGMEA 14 | 18 |
| Embodiment 3 | 2 | PGDE 0.62 | 0.052 | PGMEA 15 | 21 |
| Embodiment 4 | 2 | BGDE 0.68 | 0.054 | PGMEA 16 | 22 |
| Embodiment 5 | 2 | 1,3-DEEB 1.20 | 0.064 | PGMEA 17 | 42 |
| Embodiment 6 | 2 | EGDE 0.44 | 0.122 | PGMEA 24.4 | 28 |
| Embodiment 7 | 2 | EGDE 0.80 | 0.084 | EGME 9.4 | 23 |
| Embodiment 8 | 2 | EGDE 0.55 | 0.051 | EGME 13 | 21 |
| Embodiment 9 | 2 | DEGDE 0.76 | 0.055 | EGME 14 | 19 |
| Embodiment 10 | 2 | PGDE 0.62 | 0.052 | EGME 15 | 22 |
| Embodiment 11 | 2 | EGDE 1.10 | 0.016 | EGME 15 | 24 |
| Embodiment 12 | 2 | BGDE 0.68 | 0.054 | EGME 16 | 23 |
| Embodiment 13 | 2 | 1,3-DEEB 1.20 | 0.064 | EGME 17 | 37 |

In the above table 1, the dosages of the cyclopentenyl pimaric acid and the divinyl ether are represented by mass. After being calculated, the mole ratios thereof all fall into the range of 5:4-1:2, and even the preferable range 1:1-2:3.

It may be seen from the above table 1 that the sensitivity of the positive photoresist according to the invention is in the range of from about 18 to about 42 mJ/cm$^{-2}$, which exhibits a good sensitivity. Therefore, it can be appreciated that the positive photoresist according to the present invention has a good transparency in the deep-ultraviolet band.

The above descriptions are only illustrative for the invention, rather than being limitative. Moreover, various modifications, variations or equivalents may be made by one of ordinary skills in the art without departing from the spirit and scope of the invention as defined by the appended claims, and all these modifications, variations and equivalents fall into the protection scope of the invention.

What is claimed is:

1. A positive photoresist, comprising a cyclopentenyl pimaric acid, a divinyl ether, a photoacid generator and an organic solvent, wherein the cyclopentenyl pimaric acid is represented by the following formula:

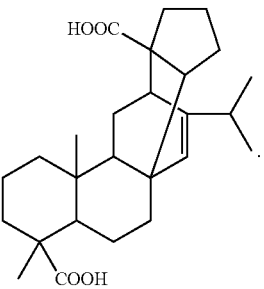 [SMILES: CC(C)C1=CC23CCC4C(C)(C(=O)O)CCCC4(C)C2CC1C1(C(=O)O)CCCC31]

2. The positive photoresist according to claim 1, wherein the divinyl ether is at least one selected from the group consisting of ethylene glycol divinyl ether, propylene glycol divinyl ether, butylene glycol divinyl ether, diethylene glycol divinyl ether, 1,3-di-(ethyleneoxy ethoxy)benzene, 1-methyl-1,2-diethyleneoxy ethane and 1,7-di-(ethyleneoxy ethoxy)naphthalene.

3. The positive photoresist according to claim 2, wherein, the divinyl ether is ethylene glycol divinyl ether, propylene glycol divinyl ether, diethylene glycol divinyl ether, or 1,3-di-(ethyleneoxy ethoxy)benzene.

4. The positive photoresist according to claim 1, wherein the photoacid generator is at least one selected from the group consisting of triphenylsulfonium trifluoromethanesulphonate, S-(2-naphthoyl)methyltetrahydrothiophenium trifluoromethanesulphonate, tri(4-methylphenyl)sulfonium trifluoromethanesulphonate, heptafluoropropane sulphonate, (4-methylphenyl)diphenyl trifluoromethanesulphonate, (p-tert-butylphenyl)diphenylsulfonium trifluoromethanesulphonate and tri(p-tert-butylphenyl)sulfonium trifluoromethanesulphonate.

5. The positive photoresist according to claim 4, wherein the photoacid generator is triphenylsulfonium trifluoromethanesulphonate.

6. The positive photoresist according to claim 1, wherein the organic solvent is at least one selected from the group consisting of acetone, methylethylketone, cyclohexanone, ethylene glycol monoethyl ether, ethylene glycol monoacetate, diethylene glyol, propylene glycol, propylene glycol monoacetate, methyl lactate, propylene glycol methyl ether acetate and ethylene glycol methyl ether acetate.

7. The positive photoresist according to claim 1, wherein the mole ratio of the cyclopentenyl pimaric acid to the divinyl ether is in the range of from about 5:4 to about 1:2.

8. The positive photoresist according to claim 3, wherein the mole ratio of the cyclopentenyl pimaric acid to the divinyl ether is in the range of from about 5:4 to about 1:2.

9. The positive photoresist according to claim 3, wherein the mole ratio of the cyclopentenyl pimaric acid to the divinyl ether is in the range of from about 1:1 to about 2:3.

10. The positive photoresist according to claim 1, wherein the photoacid generator is 0.5%-5% of the total mass of the cyclopentenyl pimaric acid and the divinyl ether.

11. The positive photoresist according to claim 3, wherein the photoacid generator is 0.5%-5% of the total mass of the cyclopentenyl pimaric acid and the divinyl ether.

12. The positive photoresist according to claim 5, wherein the photoacid generator is 0.5%-5% of the total mass of the cyclopentenyl pimaric acid and the divinyl ether.

13. The positive photoresist according to claim 10, wherein the photoacid generator is 1.0%-3.0% of the total mass of the cyclopentenyl pimaric acid and the divinyl ether.

14. The positive photoresist according to claim 1, wherein the total mass of the photoacid generator, the cyclopentenyl pimaric acid and the divinyl ether is in the range of from about 10% to about 35% by mass of the organic solvent.

15. The positive photoresist according to claim 3, wherein the total mass of the photoacid generator, the cyclopentenyl pimaric acid and the divinyl ether is in the range of from about 10% to about 35% by mass of the organic solvent.

16. The positive photoresist according to claim 5, wherein the total mass of the photoacid generator, the cyclopentenyl pimaric acid and the divinyl ether is in the range of from about 10% to about 35% by mass of the organic solvent.

17. The positive photoresist according to claim 14, wherein the total mass of the photoacid generator, the cyclopentenyl pimaric acid and the divinyl ether is in the range of from about 10 to about 30% by mass of the organic solvent.

18. The positive photoresist according to claim 1, wherein the cyclopentenyl pimaric acid is prepared according to the process comprising the following steps:
heating a gum resin to a temperature of from about 210° C. to 250° C., adding cyclopentenecarboxylic acid dropwise in a nitrogen atmosphere, carrying out the reaction at the temperature of from 210° C. to 250° C. after adding of cyclopentenecarboxylic acid is completed, and obtaining a crude product of cyclopentenyl pimaric acid after the reaction is completed; and
washing the crude product with a detergent and thus obtaining a product of cyclopentenyl pimaric acid.

19. The positive photoresist according to claim 18, wherein the detergent is at least one selected from the group consisting of carbon tetrachloride, trichloromethane, acetone, cyclohexanone and ether.

20. A cyclopentenyl pimaric acid which is represented by the following formula:

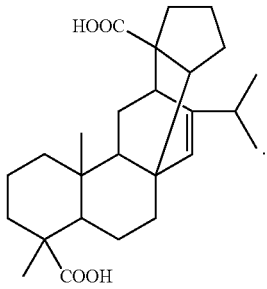 [SMILES: CC(C)C1=CC23CCC4C(C)(C(=O)O)CCCC4(C)C2CC1C1(C(=O)O)CCCC31]

* * * * *